United States Patent [19]

Wade et al.

[11] 4,104,388
[45] Aug. 1, 1978

[54] 3-SUBSTITUTED BENZISOTHIAZOLE, 1,1-DIOXIDES

[75] Inventors: Peter C. Wade, Pennington; Thomas P. Kissick, Princeton, both of N.J.

[73] Assignee: E. R. Squibb & Sons, Inc., Princeton, N.J.

[21] Appl. No.: 799,879

[22] Filed: May 23, 1977

[51] Int. Cl.$^2$ ................... A61K 31/495; C07D 417/04
[52] U.S. Cl. ................... 424/250; 260/293.57; 260/294.8 C; 260/301; 424/263; 424/267; 544/368
[58] Field of Search ........ 260/268 BC, 301 R, 293.57, 260/294.8 C; 424/250, 263, 267

[56] References Cited

U.S. PATENT DOCUMENTS 2,751,392  6/1956  Grogan et al. ................... 260/301

OTHER PUBLICATIONS

Traverso et al., *J. Med. Chem.*, (1967), vol. 10, pp. 840–844.

*Primary Examiner*—Paul M. Coughlan, Jr.
*Attorney, Agent, or Firm*—Lawrence S. Levinson; Merle J. Smith; Burton Rodney

[57] ABSTRACT

3-Substituted benzisothiazole, 1,1-dioxides are provided having the structure

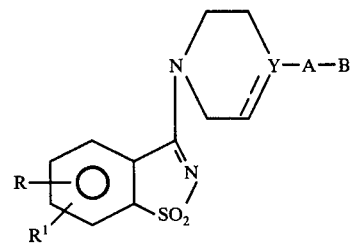

wherein R is hydrogen, halogen, lower alkyl, lower alkoxy, or nitro; $R^1$ is hydrogen, lower alkoxy or halogen with the proviso that $R^1$ can be lower alkoxy or halogen only when R is lower alkoxy or halogen, respectively; Y is C or N, where Y is C, $=\!=\!=$ may represent a double bond, and when Y is N, $=\!=\!=$ represents a single bond, A is a single bond or an alkylene group containing from 1 to 4 carbons, and B is hydrogen, hydroxyl, phenyl or phenyl substituted with halogen, lower alkyl, lower alkoxy, or trifluoromethyl, with the proviso that when Y is C, B is phenyl or substituted phenyl, and when Y is N and B is hydrogen, A has at least 1 carbon and when B is hydroxyl, A has at least 2 carbons; and physiologically acceptable acid-addition salts thereof where Y is N. These compounds are useful as antiinflammatory agents.

20 Claims, No Drawings

3-SUBSTITUTED BENZISOTHIAZOLE, 1,1-DIOXIDES

FIELD OF THE INVENTION

The present invention relates to 3-substituted benzisothiazole, 1,1-dioxides which are useful as antiinflammatory agents.

DISCUSSION OF PRIOR ART

Pyrazolyl- and pyrazolinyl-1,2-benzisothiazole, 1,1-dioxides such as 3-(3-methylpyrazol-1-yl)-1,2-benzisothiazole, 1,1-dioxide and 3-(4-acetyl-3-methylpyrazol-1-yl)-1,2-benzisothiazole, 1,1-dioxide, are disclosed as hypotensive agents; see Traverso et al, "Hypotensive 1,2-benzisothiazole 1,1-dioxides, I. Pyrazole and Pyrazoline Derivatives," *J. Med. Chem.*, Sept. 1967, Vol. 10, pp 840–844.

U.S. Pat. No. 2,751,392 to Grogan et al discloses tertiary amine derivatives of N- and O-saccharin which are said to have been found suitable for the symptomatic relief of certain types of neuralgia, rheumatoid and arthritic disorders and to possess varying degrees of anthihistaminic activity. The Grogan et al compounds are of the following three types:

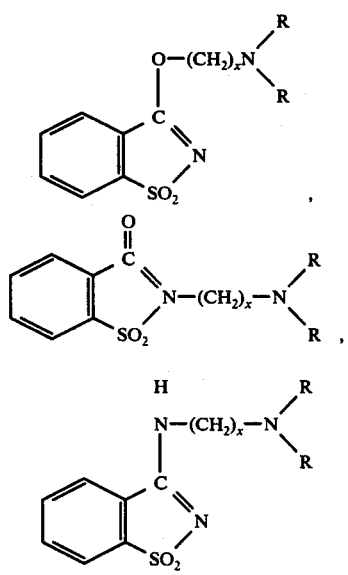

and

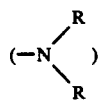

wherein x is 2 to 6, R is alkyl of 1 to 6 carbons or the grouping $(-N\diagdown_R^R)$ may represent pyrrolidine, morpholine and piperidine.

DESCRIPTION OF THE INVENTION

The 3-substituted benzisothiazole, 1,1-dioxides of the invention have the structure

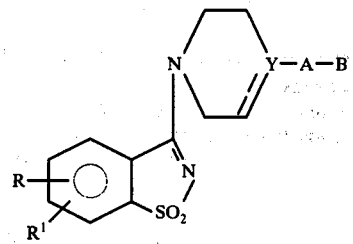

wherein R is hydrogen, halogen, lower alkyl, lower alkoxy or nitro; and $R^1$ is hydrogen, lower alkoxy or halogen, $R^1$ can be lower alkoxy or halogen only when R is lower alkoxy or halogen, respectively, R and $R^1$ in such case preferably occupying the 5- and 6-positions, respectively; Y is C or N; ---- represents an optional double bond which may be present when Y is C; A represents a single bond or an alkylene radical $(CH_2)_n$ containing 1 to 4 carbons in the normal chain; and B is hydrogen, hydroxyl, phenyl, or phenyl monosubstituted with halogen, lower alkyl, lower alkoxy or trifluoromethyl; with the proviso that when Y is C, B is phenyl or substituted phenyl; and when Y is N and B is hydrogen, A must contain at least 1 carbon or when B is hydroxyl, A must contain at least 2 carbons.

Thus, the compounds of formula I of the invention may include compounds of the following structures:

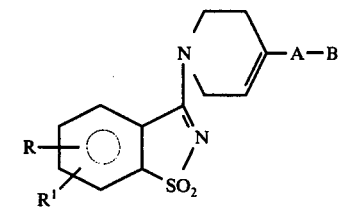

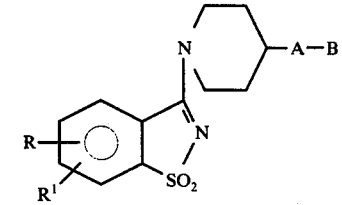

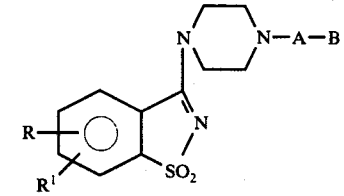

The preferred compounds of the invention are those of formula II wherein R is in the 5- or 6-position, and $R^1$ is hydrogen, or R and $R^1$ are hydrogen, A is a single bond and B is phenyl or substituted phenyl, and those of formula III wherein R is in the 5- or 6-position and $R^1$ is hydrogen or R and $R^1$ are hydrogen, A is a single bond, and B is phenyl or substituted phenyl, and those of formula IV wherein R is in the 5- or 6-position, and $R^1$ is hydrogen, or R and $R^1$ are hydrogen, A is a single bond or —$CH_2$—, or —$CH_2CH_2$—, and B is phenyl or substituted phenyl, and wherein B is H, A contains at least 1 carbon, and when B is hydroxyl, A contains at least 2 carbons.

The term "lower alkyl" as used herein refers to alkyl groups having 1 to 4 carbons, with methyl or ethyl being preferred.

The term "lower alkoxy" as used herein refers to lower alkyl groups as defined above attached to an oxygen atom, with methoxy being preferred.

The term "halogen" as employed herein refers to chlorine, bromine, iodine or fluorine with chlorine and bromine being preferred.

The compounds of Formulae I to IV of the invention may be prepared by heating a 3-substituted-1,2-benzisothiazole, 1,1-dioxide of the structure

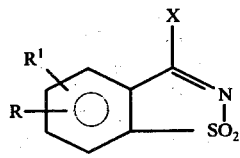

wherein X is Cl, Br, lower alkoxy, lower alkylthio, or mercapto (SH), with an amine of the structure

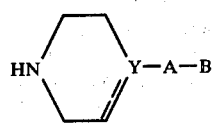

in the presence of an aprotic solvent, such as acetone, methyl ethyl ketone, dimethylformamide, hexamethylphosphoramide and the like.

The starting material V in the above reaction may be prepared by reaction of a saccharin compound of the structure

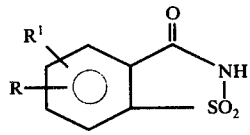

with a dehydrating agent, such as thionyl chloride in the presence of a non-reacting solvent, such as dioxane, benzene or THF in the optional presence of a catalyst, such as dimethylformamide.

The starting materials of Formula VI and VII are known in the art and may be prepared by a variety of conventional techniques.

Depending on the reaction conditions and the starting materials used, the new compounds of structure IV are obtained in the free form or in the form of their acid-addition salts. The salts thereof can be converted into the free compounds in a known manner such as by reaction with a basic agent. Free bases which may be obtained can be converted into pharmaceutically acceptable acid-addition salts by reaction with a variety of acids. Acids useful for preparing these acid-addition salts include, inter alia, inorganic acids, such as the hydrohalic acids (e.g. hydrochloric and hydrobromic acids), sulfuric acid, nitric acid, and phosphoric acid, and organic acids, such as maleic, fumaric, tartaric, citric, acetic, benzoic, 2-acetoxybenzoic, salicyclic, succinic, nicotinic, methanesulfonic or cyclohexanesulfamic.

The compounds of formula I have antiinflammatory activity as measured by the reverse passive arthus (RPA) or other related tests (M. B. Goldlust and W. F. Schreiber, *Agents and Actions*, 5, 39 (1975)) and are useful as antiinflammatory agents and may be used, for example, in a manner similar to phenylbutazone or indomethacin. They may be used to decrease joint swelling, tenderness, pain and stiffness in mammalian species, e.g., in conditions such as rheumatoid arthritis. The quantity administered ranges from about 1 mg to about 150 mg per kg of body weight per day.

For any of these pharmaceutical purposes a compound or mixture of compounds of formula I or their pharmaceutically acceptable acid-addition salts may be administered orally or parenterally in a conventional dosage form, such as tablet, capsule, injectable or the like. These may be conventionally formulated in an oral or parenteral dosage form by compounding with a conventional vehicle, excipient, binder, preservative, stabilizer, flavor or the like as called for by accepted pharmaceutical practice.

The following examples are illustrative of the invention and represent preferred embodiments. Other modifications may be readily produced by suitable variations of the reactions. All temperatures are on the Centigrade scale.

EXAMPLE 1

3-(4-Phenyl-1-piperazinyl)-1,2-benzisothiazole, 1,1-dioxide

A. 3-Chloro-1,2-benzisothiazole, 1,1-dioxide (Pseudo saccharin chloride)

Reference: Japanese Pat. No. 048934

100 g (545 mM) Saccharin, 100 ml thionyl chloride, 4 ml dimethylformamide (DMF) (catalyst), and 400 ml dioxane are refluxed overnight. Thionyl chloride (50 ml) and DMF (1 ml) are added to the reaction mixture which is refluxed overnight again. The reaction mixture is evaporated and the residue recrystallized from toluene: 73.4 g, m.p. 140°-145° [lit. m.p. 148°-149°].

B. 3-(4-Phenyl-1-piperazinyl)-1,2-benzisothiazole, 1,1-dioxide

Reference: U.S. Pat. No. 2,751,392

5.36 g (26.6 mM) 3-Chloro-1,2-benzisothiazole, 1,1-dioxide prepared in part A is dissolved in 50 ml acetone by brief heating. 5.0 g (29.3 mM) Phenylpiperazine, dissolved in 5 ml of acetone, is added to the solution dropwise over 5 minutes. The mixture is refluxed for 45 minutes, and the material that crystallizes out after standing for 2 hours at room temperature is filtered off and recrystallized twice from a mixture of 50 ml DMF and 200 ml dioxane containing 0.5 ml triethylamine to give 2.95 g of the title compound, yellow in color, m.p. 260°-262°.

EXAMPLE 2

3-(4-Phenyl-1-piperidinyl)-1,2-benzisothiazole, 1,1-dioxide 6.0 g (37.2 mM) 4-Phenylpiperidine, dissolved in 30 ml acetone, is added to 6.82 g (33.8 mM) 3-chloro-1,2-benzisothiazole, 1,1-dioxide (prepared as in Example 1A) dissolved in 50 ml warm acetone. The mixture is refluxed for 1 hour, the resulting preicpitate filtered out, washed with acetone and dried at 80°/vacuum to give 5.7 g of the title compound, m.p. 175°-177°.

EXAMPLE 3

3-(3,6-Dihydro-4-phenyl-1(2H)-pyridinyl)-1,2-benzisothiazole, 1,1-dioxide 4.8 g (30.7 mM) 4-Phenyl-1,2,3,6-tetrahydropyridine, dissolved in 20 ml acetone, is added dropwise to 5.62 (27.9 mM) 3-chloro-1,2-benzisothiazole, 1,1-dioxide (prepared as described in Example 1A) dissolved in 70 ml acetone. The mixture is refluxed for 2 hours, stirred overnight at room temperature, and the resulting precipitate filtered out. The filter cake is recrystallized twice from a mixture of 25 ml DMF and 200 ml dioxane and once from a mixture of 25 ml DMF and 50 ml ethanol containing 0.5 ml triethylamine to give 2.05 g of the title compound, m.p. 272°–273°.

The mother liquors from the recrystallizations are evaporated and the residue recrystallized from a mixture of 25 ml DMF and 200 ml ethanol containing 0.5 ml triethylamine to give 3.3 g of less pure title compound, m.p. 269°–271°.

EXAMPLE 4

4-(1,2-Benzisothiazol-3-yl)-1-piperazineethanol, S,S-dioxide, hydrochloride (1:1)

3.87 g (29.8 mM) Hydroxyethylpiperazine, dissolved in 50 ml of dioxane, is added to 6.0 g (29.8 mM) 3-chloro-1,2-benzisothiazole, 1,1-dioxide (prepared as described in Example 1A), dissolved in 100 ml of acetone, dropwise over 15 minutes. The mixture is refluxed for 30 minutes, allowed to stand at room temperature for 2 hours, and the resulting precipitate filtered out, washed with acetone, and dried at 80°/vacuum to give 9.6 g of the title compound, m.p. 270°–271°.

EXAMPLE 5

3-(4-Methyl-1-piperazinyl)-1,2-benzisothiazole, 1,1-dioxide, hydrochloride (1:1)

Reference: Tetrahedron, 30 875 (1974)

10.0 g (54.6 mM) Saccharin and 10.9 g (109.2 mM) N-methylpiperazine are refluxed in 50 ml of hexamethylphosphoramide for 6.5 hours, and the reaction mixture is allowed to stand overnight at room temperature. The resulting precipitate is filtered off, washed with 100 ml toluene, to yield N,N-dimethyl-1,2-benzisothiazole-3-amine 1,1-dioxide. After standing for a day the combined filtrate and toluene washings yield the crystalline product which is filtered off, washed with toluene, and recrystallized from toluene. The resulting free base (3-(4-methyl-1-piperazinyl)-1,2-benzoisothiazole, 1,1-dioxide) is taken up in hot ethyl acetate and shaken with 10% aqueous HCl. The precipitated salt is filtered from the two phases, washed with ethyl acetate, and dried at 80°/vacuum to give 3.9 g of the title compound, m.p. 323°–324°.

EXAMPLES 6 to 20

Following the procedure of Example 1, but substituting for the phenylpiperazine, the compound shown in Column I of Table A below, and substituting for 3-chloro-1,2-benzisothiazole, 1,1-dioxide, the compound shown in Column II, the compound of the invention shown in Column III is obtained.

TABLE A

| Ex. No. | Column I | Column II | | | Column III |
|---|---|---|---|---|---|
| | | R (position) | R¹ (position) | X | R (position), R¹ (position), —N⟩Y—A—B |
| 6. | HN⟩—(CH₂)₂—⟨OCH₃⟩ | NO₂(5) | H | Cl | As in Column II / As in Column I |
| 7. | HN⟩—⟨CH₃⟩ | NO₂(4) | H | Br | |
| 8. | HN⟩—⟨Cl⟩ | Cl(5) | H | Cl | |

TABLE A-continued

| | | Column II | | | Column III | | |
|---|---|---|---|---|---|---|---|
| Ex. No. | Column I (HN⌒Y—A—B) | R (position) | R¹ (position) | X | R (position) | R¹ (position) | (—N⌒Y—A—B) |
| | | | | | \{ As in Column II \} | | \{ As in Column I \} |
| 9. | HN⌒N—CH₂—C₆H₄(CF₃) | Cl(7) | H | Cl | | | |
| 10. | HN⌒N—(CH₂)₃CH | Cl(5) | Cl(6) | Cl | | | |
| 11. | HN⌒N(CH₂)₃CH₃ | Br(6) | H | CH₃ | | | |
| 12. | HN⌒N(CH₂)₃—C₆H₅ | F(5) | H | O(6) | | | |
| 13. | HN⌒N—C₆H₄(CF₃) | CH₃(6) | H | CH₃O | | | |
| 14. | HN⌒CH₂—C₆H₅ | i-propyl(6) | H | CH₃O | | | |
| 15. | HN⌒(CH₂)₂—C₆H₄—CH₃ | CH₃O(5) | H | Cl | | | |
| 16. | HN⌒C₆H₅ | Cl(5) | Cl(6) | Cl | | | |
| 17. | HN⌒(CH₂)₂—C₆H₅ | CH₃O(5) | CH₃(6) | Cl | | | |
| 18. | HN⌒N—(CH₂)₂—OH | NO₂(7) | H | Br | | | |
| 19. | HN⌒N—CH₂—C₆H₅ | CH₃(6) | H | Cl | | | |
| 20. | HN⌒(CH₂)₂—C₆H₅ | CH₃(7) | H | Cl | | | |

What is claimed is:

1. A compound of the structure

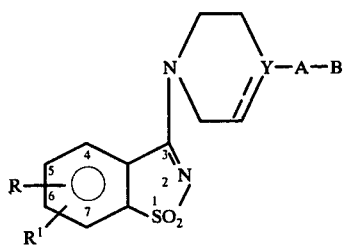

wherein R is hydrogen, halogen, lower alkyl, lower alkoxy, or nitro, R¹ is hydrogen, lower alkoxy or halogen with the proviso that R¹ can be lower alkoxy or halogen only when R is lower alkoxy or halogen, respectively; Y is C or N, where Y is C,═══ represents a single bond or a double bond, and when Y is N,═══ represents a single bond, A is a single bond or an alkylene group containing from 1 to 4 carbons, and B is hydrogen, hydroxyl, phenyl or phenyl substituted with halogen, lower alkyl, lower alkoxy, or trifluoromethyl, with the proviso that when Y is C, B is phenyl or substituted phenyl, and when Y is N and B is hydrogen, A has at least 1 carbon and when B is hydroxyl, A has at least 2 carbons; and physiologically acceptable acid-addition salts thereof where Y is N.

2. The compound of claim 1 having the structure

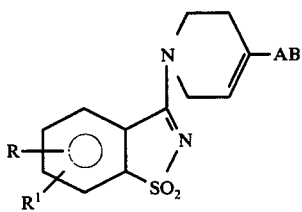

3. The compound of claim 1 having the structure

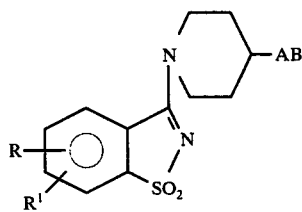

4. The compound of claim 1 having the structure

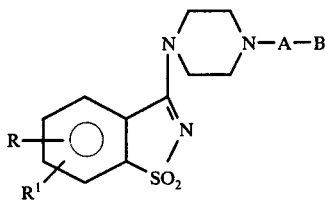

5. The compound of claim 1 wherein R¹ is H.

6. The compound of claim 1 wherein R is in the 5- or 6-position and R¹ is H.

7. The compound of claim 1 wherein R¹ is lower alkoxy or halogen, and R is lower alkoxy or halogen.

8. The compound of claim 7 wherein R and R¹ occupy the 5- and 6-positions, respectively.

9. The compound of claim 2 wherein B is phenyl or substituted phenyl.

10. The compound of claim 3 wherein B is phenyl or substituted phenyl.

11. The compound of claim 4 wherein B is phenyl or substituted phenyl.

12. The compound of claim 4 wherein B is hydrogen, A has at least 1 carbon or B is hydroxyl and A has at least 2 carbons.

13. The compound of claim 9 wherein R and R¹ are H, and A is a single bond.

14. The compound of claim 10 wherein R and R¹ are H and A is a single bond.

15. The compound of claim 4 wherein R and R¹ are H, A is a single bond, CH₂ or (CH₂)₂ and B is phenyl.

16. The compound of claim 12 wherein A is —(CH₂)₂— and B is hydroxyl.

17. The compound of claim 4 wherein A is a single bond and B is phenyl.

18. A compound as defined in claim 1 having the name 3-(4-phenyl-1-piperazinyl)-1,2-benzisothiazole, 1,1-dioxide, 3-(3,6-dihydro-4-phenyl-1(2H)-pyridinyl)-1,2-benzisothiazole, 1,1-dioxide, 4-(1,2-benzisothiazol-3-yl)-1-piperazineethanol, S,S-dioxide hydrochloride, or 3-(4-methyl-1-piperazinyl)-1,2-benzisothiazole, 1,1-dioxide hydrochloride.

19. A composition for treating an inflammatory condition which comprises an effective amount of a compound of claim 1 in a physiologically acceptable vehicle.

20. A method for treating an inflammatory condition in a mammalian host, which comprises administering an effective amount of the composition of claim 19.

* * * * *